US00PP28830P3

(12) United States Plant Patent
Ceballos

(10) Patent No.: US PP28,830 P3
(45) Date of Patent: Dec. 26, 2017

(54) ***SENECIO* PLANT NAMED 'SENAW'**

(50) Latin Name: *Senecio candicans*
Varietal Denomination: Sennova 0012015

(71) Applicant: Floricultura Novazel S.A., Santiago (CL)

(72) Inventor: Matias Eduardo Avendano Ceballos, Santiago (CL)

(73) Assignee: FLORICULTURA NOVAZEL S.A., Santiago (CL)

( * ) Notice: Subject to any disclaimer, the term of this patent is extended or adjusted under 35 U.S.C. 154(b) by 61 days.

(21) Appl. No.: 14/998,799

(22) Filed: Feb. 17, 2016

(65) Prior Publication Data

US 2017/0238453 P1 Aug. 17, 2017

(30) Foreign Application Priority Data

Jul. 21, 2015 (QZ) ..... PBR 2015/1567

(51) Int. Cl.
*A01H 5/12* (2006.01)

(52) U.S. Cl.
USPC ..... Plt./480

(58) Field of Classification Search
USPC ..... Plt./263.1, 480
See application file for complete search history.

*Primary Examiner* — June Hwu
*Assistant Examiner* — Karen Redden
(74) *Attorney, Agent, or Firm* — Penny J. Aguirre

(57) ABSTRACT

A new cultivar of *Senecio* plant, 'Senaw', characterized by its leaves that are broadly ovate in shape, unlobed with wavy crenate margins, silvery white in color due to its densely wolly tomentose surface, its foliage that retains its coloration for a long period during the growing season, and its ease of propagation.

3 Drawing Sheets

Botanical classification: *Senecio candicans.*
Variety denomination: 'Senaw'.

BACKGROUND OF THE INVENTION

The present invention relates to a new and distinct cultivar of *Senecio* plant, botanically known as *Senecio candicans* 'Senaw' and will be referred to hereafter by its cultivar name, 'Senaw'. The new cultivar represents a new dusty miller grown as an annual for bedding and container use.

The new cultivar resulted from on ongoing breeding program by the Inventor at his nursery in Puerto Montt, Chile with the objective of selecting a new cultivars of *Senciao candicans* with unique leaf shapes and colors and plant habits. 'Senaw' arose from open pollination of an unnamed and unpatented plant of *Senecio candicans* and therfore the male parent is unknown. The Inventor selected the new cultivar as a single unique plant from the resulting seedlings in the summer of 2010.

Asexual propagation of the new cultivar was first accomplished by division in Puerto Montt, Chile in May of 2011 by the Inventor. Asexual propagation by division, root cuttings and tissue culture has determined that the characteristics of this cultivar are stable and are reproduced true to type in successive generations.

SUMMARY OF THE INVENTION

The following traits have been repeatedly observed and represent the characteristics of 'Senaw'. These attributes in combination distinguish 'Senaw' as a new and distinct cultivar of *Senecio.*

1. 'Senaw' exhibits leaves that are broadly ovate and unlobed with wavy crenate margins.

2. 'Senaw' exhibits leaves that are silvery white in color due to its densely wolly tomentose surface.
3. 'Senaw' exhibits leaves that retains its coloration for a long period during the growing season.
4. 'Senaw' exhibits a moderately vigorous growth habit.
5. 'Senaw' has been shown to be readily propagated.

The female parent of 'Senaw', differs from 'Senaw' in having a slower growth habit and in having leaves that are less white in color with poorer color retention during the growth season and that differs in shape. 'Senaw' can also be compared to cultivars of dusty miller; *Brachyglottis greyi* 'Sunshine' (not patented) and *Senecio cineraria* 'Silver Dust' (not patented). 'Sunshine' is similar to 'Senaw' in having foliage that is silver-grey in color. 'Sunshine' differs from 'Senaw' in having leaves that are much smaller in size, in having a woody shrub plant habit and in being more floriferous. 'Silver Dust' is similar to 'Senaw' in having foliage that is silver-grey in color. 'Silver Dust' differs from 'Senaw' in having leaves that are pinnately lobed.

BRIEF DESCRIPTION OF THE DRAWINGS

The accompanying colored photographs illustrate the overall appearance and distinct characteristics of the new *Senecio*. The photographs were taken of a six month-old plant of 'Senaw' as grown in a cold greenhouse in a 3-liter container in Lisse, The Netherlands.

The photograph in FIG. 1 is a view of a plant of 'Senaw'.

Figure 1:
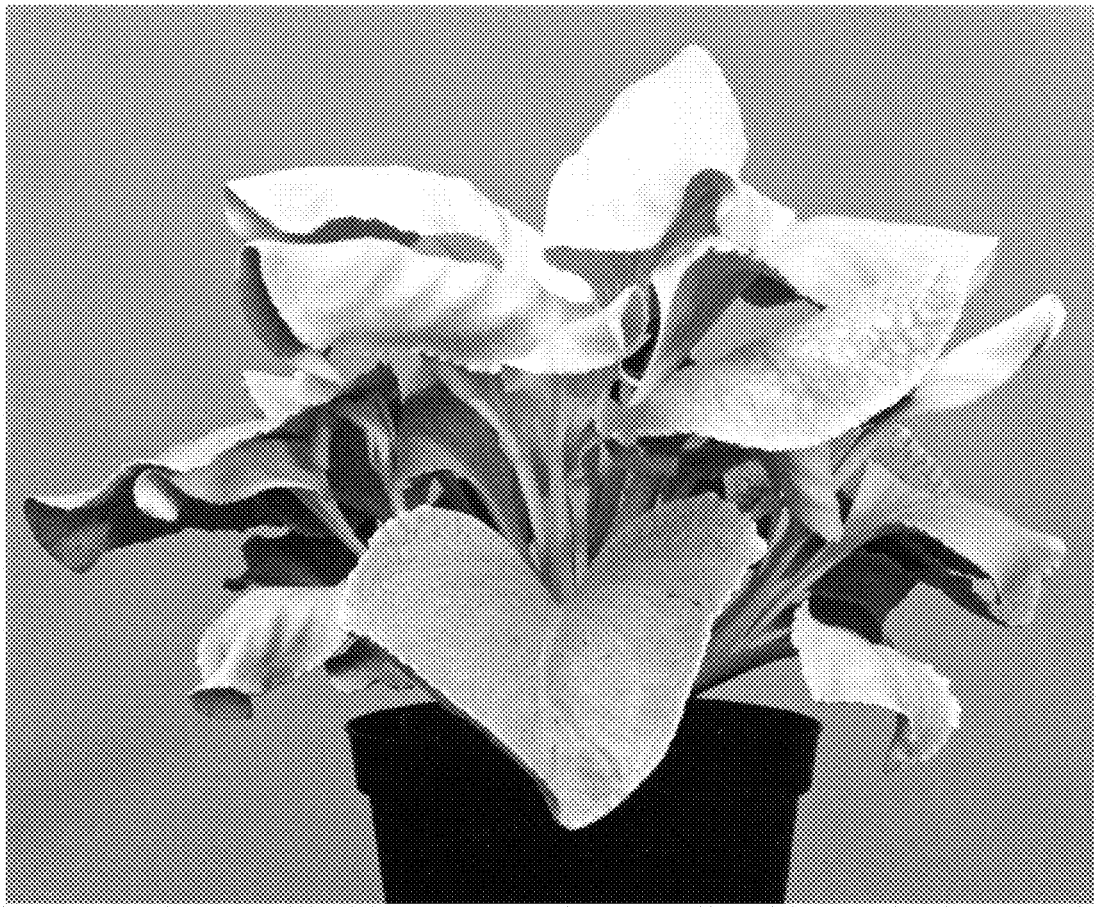
Figure 2:
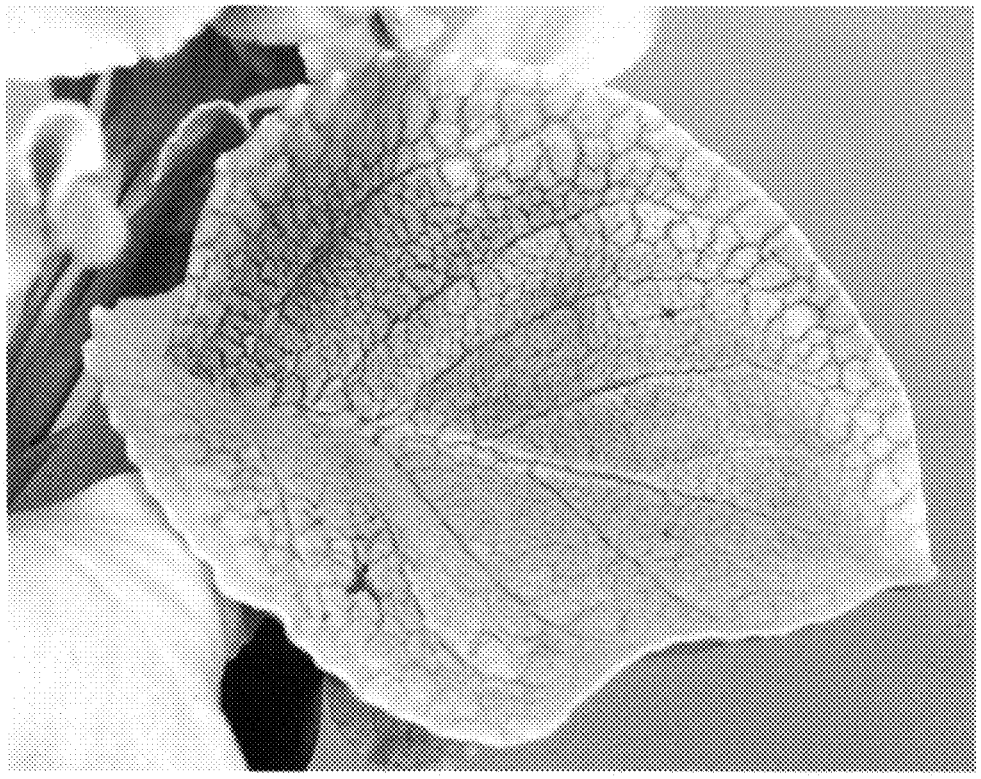

The photograph in FIG. 2 is a close-up view of a mature leaf of 'Senaw'.

Figure 3:
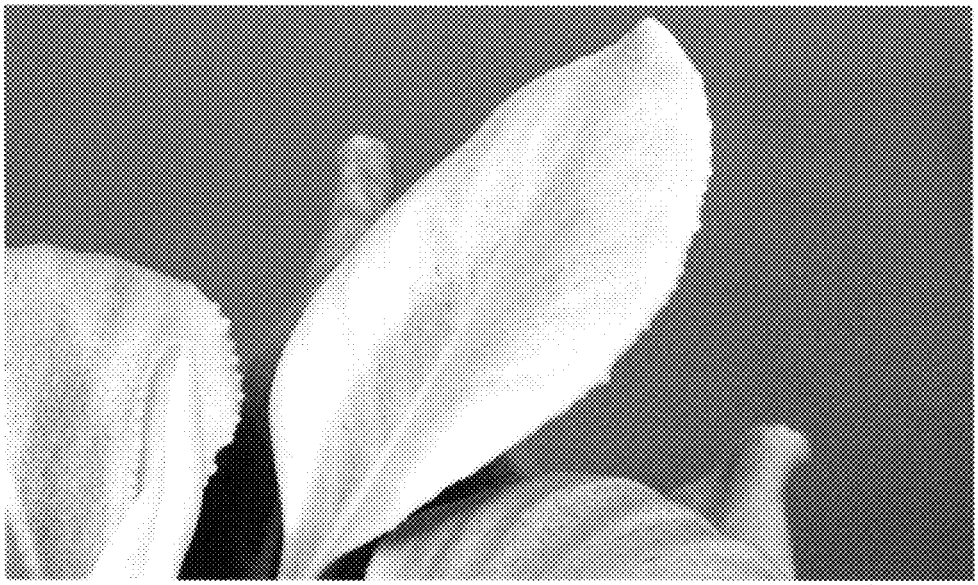

The Photograph in FIG. 3 provides a close-up view of a young leaf of 'Senaw'.

Figure 4:
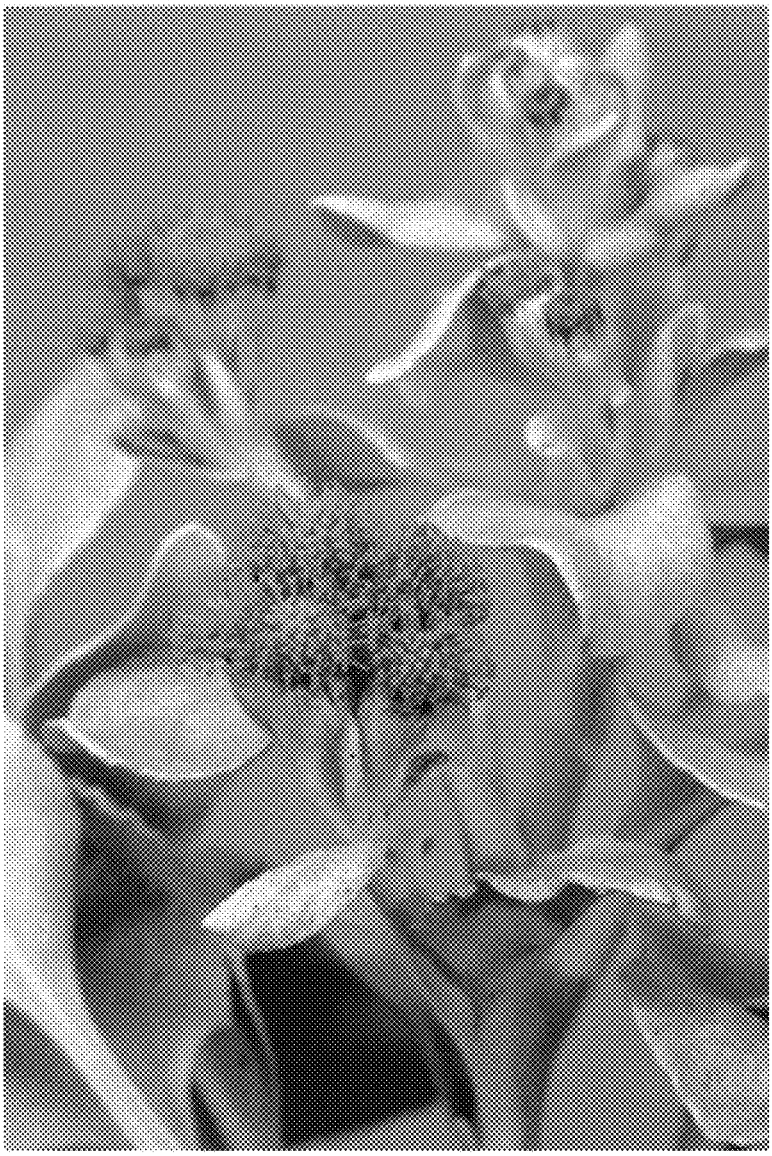

The photograph in FIG. 4 provides a view of the inflorescences of 'Senaw'.

The colors in the photographs may differ slightly from the color values cited in the detailed botanical description, which accurately describe the colors of the new *Senecio*.

DETAILED BOTANICAL DESCRIPTION

The following is a detailed description of six month-old plants of the new cultivar as grown in 3-liter circular containers in a greenhouse in Lisse, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Early July to September in The Netherlands.

*Plant habit.*—Herbaceous perennial, upright and broadly spreading.

*Height and spread.*—An average of 50 cm in height and 60 cm in width as a six month-old plant.

*Cold hardiness.*—At least to U.S.D.A. Zone 8.

*Diseases and pests.*—No susceptibility or resistance to diseases or pests has been observed.

*Root description.*—Fibrous.

*Propagation.*—Division, root cuttings, and tissue culture.

*Growth rate.*—Moderately vigorous.

*Root development.*—6 to 8 weeks from a rooted cutting or a tissue culture plug.

Stem description:

*Stem color.*—144A and covered with tomentose NN155C in color.

*Stem size.*—Average of 6 cm in length and 9 mm in diameter.

*Stem surface.*—Very densely wooly and tomentose NN155C in color.

*Branching habit.*—Freely branching, strong, 1 basal branches, pinching not required, but will improve branching.

*Internode length.*—Average of 1.1 cm.

Foliage description:

*Leaf division.*—Simple.

*Leaf arrangement.*—Alternate.

*Leaf shape.*—Broadly ovate.

*Leaf size.*—Average of 17.2 cm in length and 16 cm in width.

*Leaf number.*—Average of 6 per lateral branch.

*Leaf base.*—Broad attenuate.

*Leaf apex.*—Rounded.

*Leaf margin.*—Crenulate and wavy.

*Leaf venation.*—Pinnate, upper surface color; 146D, densely covered with woolly tomentose 194D in color, lower surface color; vein surface color not visible due to densely woolly tomentose, N155A and NN155D in color.

*Leaf surface.*—Upper surface has a slight sheen, both sides densely wolly tomentose N155A and NN155D in color.

*Leaf substance.*—Leathery.

*Leaf color.*—Leaf color is defined by the very dense woolly tomentose, young upper and lower surface; color between N155A and NN155D, mature upper surface; color between N155A and 198D, mature lower surface; color between N155A and NN155D.

*Petioles.*—Sulcate in shape, average of 10.8 cm in length and 1.1 cm in diameter, upper surface; 146D in color with surface is densely covered with wolly tomentose 194D in color, lower surface; color defined by wooly tomentose surface N155A and NN155D in color.

*Foliage fragrance.*—Mild mint scent if crushed.

Flower description:

*Inflorescence type.*—Terminal and axillary cymes of capitulae.

*Lastingness of inflorescence.*—Average of 10 days, persistant.

*Fragrance.*—Sweet and slightly musty.

*Quantity of inflorescences.*—Free flowering, with an average of 36 capitulums per plant.

*Inflorescence size.*—Cyme; 3.8 cm in height, 4 cm in diameter, capitulum; 2.1 cm in height, 2 cm in diameter.

*Inflorescence aspect.*—An average angle of 25° to peduncle.

*Inflorescence buds.*—Broad ovate in shape with a flattened top, an average of 1.1 cm in depth and 1 cm in diameter, surface is heavily pubescent with woolly tomentose hairs, color in between N155A and NN155D, immature disc florets 151C in color.

*Peduncle.*—Rounded in shape, moderately strong, and average of 3.1 cm in length and 2 mm in diameter, held on top of main flowering stem, secondary penduncle held at an average of 25°, surface is very densely covered with tomentose hairs with a color between N155A and NN155D.

Involucral bracts:

*Involucral number.*—Average of 20, placed around disc in 1 row.

*Involucral arrangement.*—Spirally placed around disc.

*Involucral size.*—An average of 8 mm in length, 2 mm in width.

*Involucral color.*—Upper surface 144C, tip 144B, lower surface densely covered with woolly tomentose hairs, between N155A and NN155D in color.

*Involucral texture.*—Upper surface glabrous and smooth, lower surface densely pubescent covered with woolly tomentose hairs, between N155A and NN155D in color.

*Involucral apex.*—Narrowly acute.

*Involucral base.*—Cuneate.

*Involucral shape.*—Narrow ovate to linear.

*Involucral magins.*—Entire.

Ray Florets (none present).

Disk florets:

*Number.*—An average of 70.

*Shape.*—Tubular, spirally placed on disc, fused into tube, upper 20% free.

*Aspect.*—Upright.

*Size.*—Average of 1.4 cm in length and 4 mm in width.

*Apex.*—Acute.

*Margins.*—Entire.

*Texture.*—Both surfaces are gloubrous and moderately glossy.

*Color.*—Upper and lower surface when opening; top 5B, mid-section 5C, base between 150C and 150D, upper and lower surface when fully open; top 3A to 3B, mid-section 3C, base between 150C and 150D.

*Receptacle.*—An average of 3 mm in depth and width, inverted deltoid in shape, 147D in color.

Reproductive Organs:

*Presence.*—Disk flowers only.

*Gynoecium.*—1 Pistil, an average of 1.1 cm in length, stigma; unequal, decurrent, 0.8 mm in length, 1.5 mm in diameter, 14B in color, style; 9 mm, 150D in color, ovary; 145D in color.

*Androecium.*—5 stamens, anther; basifixed, linear, 3 mm in length, 0.3 mm in width, 200A in color, filament; 3 mm in length 150D in color, pollen; moderate in quantity, 17B in color.

*Seed.*—No seed development was observed, have been observed to be sterile.

It is claimed:

1. A new and distinct variety of *Senecio* plant designated 'Senaw' as described and illustrated herein.

* * * * *